US011830580B2

(12) United States Patent
Kaufman et al.

(10) Patent No.: US 11,830,580 B2
(45) Date of Patent: Nov. 28, 2023

(54) K-MER DATABASE FOR ORGANISM IDENTIFICATION

(71) Applicants: International Business Machines Corporation, Armonk, NY (US); Mars, Incorporated, McClean, VA (US)

(72) Inventors: James H. Kaufman, San Jose, CA (US); Matthew A. Davis, San Jose, CA (US); Mark Kunitomi, San Francisco, CA (US); Bart C. Weimer, Davis, CA (US)

(73) Assignees: International Business Machines Corporation, Armonk, NY (US); Mars, Incorporated, McClean, VA (US)

( * ) Notice: Subject to any disclaimer, the term of this patent is extended or adjusted under 35 U.S.C. 154(b) by 1120 days.

(21) Appl. No.: 16/147,779

(22) Filed: Sep. 30, 2018

(65) Prior Publication Data
US 2020/0104464 A1    Apr. 2, 2020

(51) Int. Cl.
| G16B 30/00 | (2019.01) |
| G06F 16/28 | (2019.01) |
| G16B 20/00 | (2019.01) |
| G16B 30/10 | (2019.01) |

(52) U.S. Cl.
CPC ........... G16B 30/00 (2019.02); G06F 16/285 (2019.01); G16B 20/00 (2019.02); G16B 30/10 (2019.02)

(58) Field of Classification Search
CPC ........ G16B 20/00; G16B 30/00; G06F 16/285
See application file for complete search history.

(56) References Cited

U.S. PATENT DOCUMENTS

| 2015/0294065 A1 | 10/2015 | Gautier et al. | |
| 2016/0103958 A1* | 4/2016 | Hebert .................... | G16B 10/00 707/737 |
| 2016/0132640 A1* | 5/2016 | Layer ...................... | G16B 40/00 706/12 |

FOREIGN PATENT DOCUMENTS

WO    2016203246 A1    12/2016

OTHER PUBLICATIONS

Wei, D., Jiang, Q., Wei, Y. and Wang, S., 2012. A novel hierarchical clustering algorithm for gene sequences. BMC bioinformatics, 13(1), pp. 1-15. (Year: 2012).*
McDonald, D., Price, M.N., Goodrich, J., Nawrocki, E.P., DeSantis, T.Z., Probst, A., Andersen, G.L., Knight, R. and Hugenholtz, P.. An improved Greengenes taxonomy with explicit ranks for ecological and evolutionary analyses of bacteria and archaea. The ISME journal, 6(3), pp. 610-618. (Year: 2012).*
Ainsworth et al., "k-SLAM: accurate and ultra-fast taxonomic classification and gene identification for large metagenomic data sets," Nucleic Acids Research, 2017, vol. 45, No. 4, 1649-1656.
Asnicar et al., "Compact graphical representation of phylogenetic data and metadata with GraPhlAn," PeerJ, 2015, 3:e1029, p. 1-17.
Bacci, "Raw Sequence Data and Quality Control,", Bacterial Pangenomics: Methods and Protocols, Methods in Molecular Biology, Alessio Mengoni et al. (eds.), © Springer Science+Business Media New York 2015, vol. 1231, Chapter 9, p. 137-149.
Chojnacki et al., "Programmatic access to bioinformatics tools from EMBL-EBI update: 2017," Nucleic Acids Research, 2017, vol. 45, W550-W553.
Edgar, "MUSCLE: a multiple sequence alignment method with reduced time and space complexity," BMC Bioinformatics 2004, 5:113, 1-19.
Edgar, "MUSCLE: a multiple sequence alignment with high accuracy and high throughput," Nucleic acids research, 2004, 32, 1792-1797.
Fahim et al., "Efficient enhanced k-means clustering algorithm," J Zhejiang Univ Science A 2006 7(10):1626-1633.
Meier-Kolthoff et al., "Genome sequence-based species delimitation with confidence intervals and improved distance functions," BMC bioinformatics 14, 1 (2013) p. 1-14.
Menzel et al., "Fast and sensitive taxonomic classification for metagenomics with Kaiju," Nat. Commun. 7:11257 (2016) p. 1-9.
Merchant et al., "Unexpected cross-species contamination in genome sequencing projects," PeerJ, 2014, 2:e675; DOI 10.7717/peerj.675 p. 1-7.
Mullner, "Modern hierarchical, agglomerative clustering algorithms," arXiv:1109.2378v1 [stat.ML] Sep. 12, 2011 p. 1-29.
Nasko et al., "RefSeq database growth influences the accuracy of k-mer-based species identification," bioRxiv preprint first posted online Apr. 19, 2018; doi: http://dx.doi.org/10.1101/304972 p. 1-21.
Ondov et al., "Mash: fast genome and metagenome distance estimation using MinHash," Genome Biology (2016) 17:132, p. 1-14.

(Continued)

Primary Examiner — Lori A. Clow
Assistant Examiner — Janna Nicole Schultzhaus
(74) Attorney, Agent, or Firm — CANTOR COLBURN LLP; James Olsen

(57) ABSTRACT

A large collection of sample genomes containing misclassified k-mers and metadata errors from a reference taxonomy was converted to a self-consistent k-mer database comprising a self-consistent taxonomy. The self-consistent taxonomy was based on genetic distances calculated using the MinHash method or the Meier-Koltoff method. An agglomerative clustering algorithm was used to calculate the self-consistent taxonomy. Each k-mer of the sample genomes was assigned to only one node of the self-consistent taxonomy. In another step, each node of the self-consistent taxonomy was mapped to the reference taxonomy, thereby preserving in the self-consistent taxonomy links to the reference taxonomy while correcting for the misclassification errors therein. The self-consistent k-mer database can be used to taxonomically profile sequenced nucleic acids with greater specificity compared to systems relying on the reference taxonomy.

19 Claims, 9 Drawing Sheets

(56) References Cited

OTHER PUBLICATIONS

Ounit et al., "CLARK: fast and accurate classification of metagenomic and genomic sequences using discriminative k-mers," BMC Genomics (2015) 16:236, p. 1-13.

Pruitt et al., "NCBI reference sequences (RefSeq): a curated non-redundant sequence database of genomes, transcripts and proteins" Nucleic Acids Research, vol. 35, Issue suppl_1, Jan. 1, 2007, pp. D61-D65.

Putnaik et al. "Divisive Analysis (DIANA) of hierarchical clustering and GPS data for level of service criteria of urban streets" Alexandria Engineering Journal (2016) 55, 407-418.

Rohlf, "Algorithm 76. Hierarchical clustering using the minimum spanning tree" The Computer Journal, Jan. 1973 16, 93-95.

Sibson, "SLINK: An optimally e cient algorithm for the single-link cluster method" The Computer Journal, Jan. 1973, 16, 30-34.

Ward, "Hierarchical Grouping to Optimize an Objective Function" Journal of the American Statistical Association, vol. 58, No. 301 (Mar. 1963), pp. 236-244.

Wood et al., "Kraken: ultrafast metagenomic sequence classification using exact alignments" Genome Biology, 2014, 15:R46 p. 1-12.

Xu et al., "A metric model of amino acid substitution" Bioinformatics 20(8) © Oxford University Press 2004, vol. 20 No. 8, 2004, pp. 1214-1221.

Auch et al., "Standard operating procedure for calculating genome-to-genome distances based on high-scoring segment pairs," Standards in Genomic Sciences (2010) 2: pp. 142-148.

Bandoy et al., "Misclassification of a whole genome sequence reference defined by the Human Micro biome Project: a detrimental carryover effect to microbiome studies," medRxiv preprint doi: https://doi.org/10.1101/19000489, posted Jul. 6, 2019, pp. 1-14.

Bremges et al., "CAMITAX: Taxon labels for microbial genomes," bio Rxiv preprint doi: https://doi.org/10.1101/532473; posted Jun. 4, 2019, pp. 1-7.

Bremges et al., "CAMITAX: Taxon labels for microbial genomes," GigaScience, 9, 2020, pp. 1-7; doi: 10.1093/gigascience/giz154.

Chen et al., "Comparative Genomics Reveals the Diversity of Restriction-Modification Systems and DNA Methylation Sites in Listeria monocytogenes," Feb. 2017, vol. 83 Issue 3, e02091-16 (pp. 1-16).

Ciufo et al., "Using average nucleotide identity to improve taxonomic assignments in prokaryotic genomes at the NCBI," Int J Syst Evol Microbiol 2018;68, pp. 2386-2392.

Eisen et al., "Evidence for symmetric chromoso mal inversions around the replication origin in bacteria," Genome Biology, 2000, 1(6):research0011.1-0011.9 (pp. 1-9).

Foutouhi et al., "Placental Microbiome of Healthy Pregnancies Exhibits Complex Microbial Interactions," Poster, Feb. 2017, downloaded Jul. 21, 2022 from https://www.researchgate.net/publication/313980289_Placental_Microbiome_of_Healthy_Pregnancies_Exhibits_Complex_Microbial_Interactions; DOI:10.13140/RG.2.2.11322.39366, pp. 1-2.

Github, "Genome Clustering," https://github.com/labgem/microscope-user-doc/blob/0edfde813dc333420c88c99a11a77293c329a4b2/docs/content/compgenomics/genoclust.rst; last edit Jun. 29, 2021; downloaded Jul. 21, 2022, pp. 1-6.

Jain et al., "A fast adaptive algorithm for computing whole-genome homology maps," Bioinformatics, 34, 2018, pp. i748-i756; doi: 10.1093/bioinformatics/bty59.

Lawton et al., "Comparative analysis of Campylobacter isolates from wild birds and chickens using MALDI-TOF MS, biochemical testing, and DNA sequencing," Journal of Veterinary Diagnostic Investigation 2018, vol. 30(3), pp. 354-361.

Mahato et al., "Microbial taxonomy in the era of OMICS: application of DNA sequences, computational tools and techniques," Antonie van Leeuwenhoek, 2017, 110, pp. 1357-1371; DOI 10.1007/s10482-017-0928-1.

MUMMER Home Page, "MUMMER 3+ Ultra-fast alignment of largescale DNA and protein sequences," downloaded Jul. 21, 2022 from http://mummer.sourceforge.net/; archived versions dating back to Jun. 18, 2005 at https://web.archive.org/web/*/http://mummer.sourceforge.net/; pp. 1-5.

Parks et al., "A proposal for a standardized bacterial taxonomy based on genome phylogeny," bioRxiv preprint doi: https://doi.org/10.1101/256800; posted Jan. 31, 2018, pp. 1-35.

Parks et al., "Selection of representative genomes for 24,706 bacterial and archaeal species clusters provide a complete genome-based taxonomy," bioRxiv preprint doi: https://doi.org/10.1101/771964; posted Nov. 4, 2019, pp. 1-25.

Popic et al., "A hybrid cloud read aligner based on MinHash and kmer voting that preserves privacy," Nature Communications, 2017, 8:15311, pp. 1-7; DOI: 10.1038/ncomms15311.

Richter et al., "JSpeciesWS: a web server for prokaryotic species circumscription based on pairwise genome comparison," Bioinformatics, 32(6), 2016, pp. 929-931.

Taff et al., "Influence of Host Ecology and Behavior on Campylobacter jejuni Prevalence and Environmental Contamination Risk in a Synanthropic Wild Bird Species," Applied and Environmental Microbiology, 2016, 82(15), pp. 4811-4820.

Varghese et al., "Microbial species delineation using whole genome sequences," Nucleic Acids Research, 2015, vol. 43, No. 14, pp. 6761-6771.

Weis et al., "Genomic Comparison of *Campylobacter* spp. and Their Potential for Zoonotic Transmission between Birds, Primates, and Livestock," Applied and Environmental Microbiology, 2016, vol. 82(24), pp. 7165-7175.

Nei, "Genetic Distance between Populations," The American Naturalist 106, No. 949 (May-Jun. 1972): pp. 283-292.

\* cited by examiner

| self-consistentID | kmer hits | ref_ID1 | prob(1) | ref_ID2 | prob(2) | ref_ID3 | prob(3) | ref_ID4 | prob(4) | ref_ID5 | prob(5) | ref_ID6 | prob(6) |
|---|---|---|---|---|---|---|---|---|---|---|---|---|---|
| 318856 | 250170 | 1350 | 1.0000 | | | | | | | | | | |
| 325910 | 247573 | 590 | 0.0003 | 1301 | 0.9997 | | | | | | | | |
| 327580 | 247153 | 590 | 0.0003 | 1301 | 0.9997 | | | | | | | | |
| 328523 | 224345 | 1279 | 0.0188 | 1350 | 0.9779 | 561 | 0.0006 | 1578 | 0.0006 | 1485 | 0.0006 | 1637 | 0.0013 |

FIG. 6

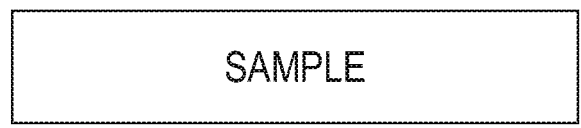
FIG. 8A
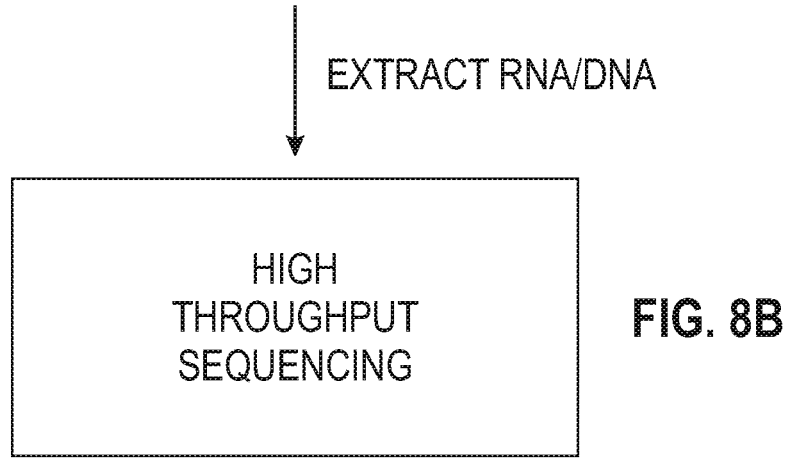
FIG. 8B
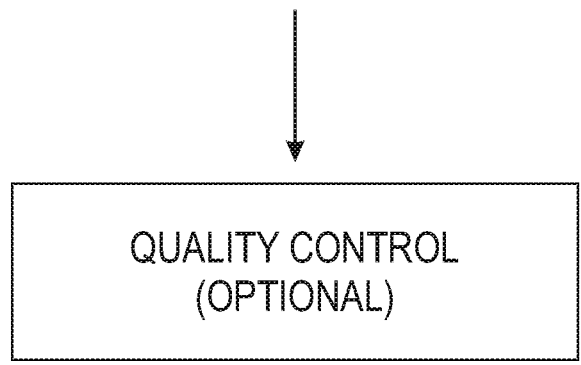
FIG. 8C
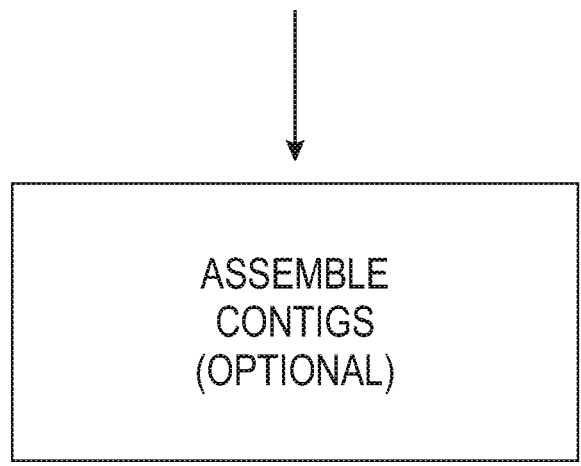
FIG. 8D
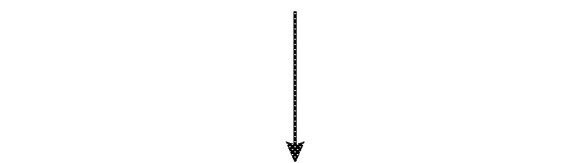

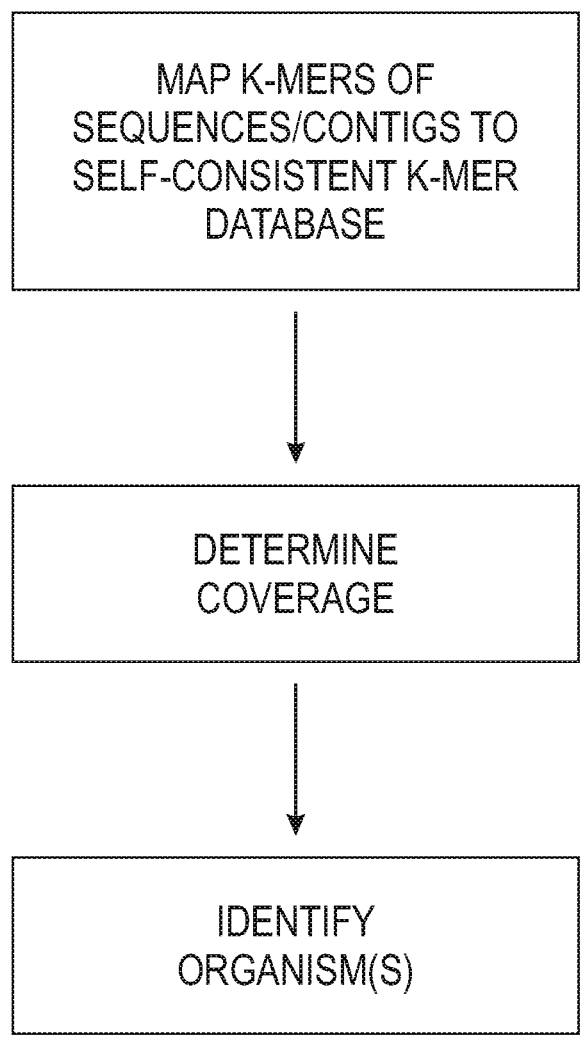

K-MER DATABASE FOR ORGANISM IDENTIFICATION

PARTIES TO A JOINT RESEARCH AGREEMENT

This invention was made under a joint research agreement between International Business Machines Corporation and Mars, Incorporated.

BACKGROUND

The present invention relates to a k-mer database for organism identification, and more specifically, to a k-mer database having a self-consistent taxonomic structure based on genetic distance.

When a patient is ill or a food product is contaminated with infectious organisms, clinicians, public health investigators, and regulators, use a variety of techniques to identify the source of illness or contamination. Next Generation Sequencing (NGS) has become cheap enough that whole genome sequencing (WGS) has been adopted by the Food and Drug Administration (FDA), Center for Disease Control (CDC), Department of Agriculture (USDA) of the US federal government. Sequencing instruments have been provided to state public health laboratories for this purpose. Academic groups use a combination of WGS, targeted gene sequencing (e.g., 16S, 18S), sequencing from isolated RNA, and other amplicon sequencing techniques to classify and compare genomes, genes, plasmids, etc., of various organisms. An amplicon is a segment of DNA or RNA that is the source and/or product of amplification or replication events. Sequencing is mandated for outbreaks associated with several pathogenic organisms known to cause foodborne disease. Mandated sequencing is expected to grow over time.

Once a pathogen is sequenced, the data can be used in several ways. For example, the similarity between genomes from several environmental and/or clinical samples has been used to declare that an outbreak is underway. In the past two years, the CDC has been able to identify related outbreaks when the sizes of the outbreaks are as small as three patients (the theoretical limit is two patients). The sequence data are also used to identify the strains of organisms as a way of determining the most effective treatment (e.g., choosing the antibiotic most likely to be effective for a specific patient).

The sequence data from food samples, patients, and environmental samples (e.g., factories) are also used to trace an outbreak back to a specific source or responsible entity (e.g., individual, organization). That entity may suffer legal and/or commercial penalties including shut down and/or financial penalties for damages resulting from an outbreak.

If the organism identification is incorrect or inaccurate, patients may not receive the correct medicine, and organizations not involved in an outbreak may be held responsible. Scientific and industrial research groups may also draw invalid conclusions in important work (e.g., drug design, primer design, etc.). For these reasons, it is essential for organism classification and naming to be accurate.

It is also essential that the computer systems and software tools used to perform classifications be fast and efficient. For this reason, many groups are adopting k-mer based classification software. In a k-mer based classification method, a reference database is constructed using a set of genomes and taxonomy provided by the user.

Standard taxonomic classification of microbes in official databases (e.g., the National Center for Biotechnology Information (NCBI) Sequence Read Archive (SRA) and NCBI Genbank) contain many errors. Metadata are in error for hundreds of organisms, with genomes receiving the wrong identification (ID). The taxonomic tree is also inaccurate and routinely changes as new genomes are added to NCBI or other public databases. This causes two problems: i) a k-mer database built with the inaccurate and error-filled standard taxonomy loses the ability to accurately identify specific taxa (e.g., genera are not named correctly) and ii) when this sub-optimal database is used to identify newly sequenced organisms, a large fraction of the sequence data from the new organisms may go unidentified or become inaccurately named, resulting in the final identification being simply wrong. An incorrect classification can lead to the wrong name at each level of the taxonomic tree.

Accordingly, a need exists for k-mer databases having a self-consistent taxonomy that is insensitive to metadata errors.

SUMMARY

Accordingly, a method is disclosed, comprising:
providing a reference database comprising k-mers derived from sequencing nucleic acids of one or more organisms, wherein the k-mers are classified to nodes of a reference taxonomy, the reference taxonomy not based on genetic distances, the nodes of the reference taxonomy representing genome classifications, the nodes of the reference taxonomy having unique reference IDs, wherein IDs means identifications;
providing a sample database comprising sample genomes that includes genomes of the one or more microorganisms,
calculating genetic distances of the sample genomes, thereby forming a distance matrix;
calculating a self-consistent taxonomy using the distance matrix;
constructing a k-mer database wherein k-mers of the sample genomes are assigned to nodes of the self-consistent taxonomy, the nodes of the self-consistent taxonomy assigned respective unique self-consistent IDs, and each of the k-mers of the sample genomes linked to a respective one of the self-consistent IDs;
mapping the reference IDs of the reference taxonomy to the self-consistent IDs of the self-consistent taxonomy, wherein each of the self-consistent IDs is linked to 1 or more of the mapped reference IDs; and
calculating respective weights and/or respective probabilities of the mapped reference IDs based on the number of nodes of the self-consistent taxonomy linked to each of the mapped reference IDs, wherein each of the mapped reference IDs of a given node of the self-consistent taxonomy is assigned a calculated weight and/or a calculated probability;
wherein
the self-consistent k-mer database is stored on a computer readable medium, and
the self-consistent k-mer database is capable of being queried for taxonomic profiling of sequenced nucleic acids when electronically linked to a computer system.

Also disclosed is a system comprising one or more computer processor circuits configured and arranged to:
provide a reference database comprising k-mers derived from sequencing nucleic acids of one or more organisms, wherein the k-mers are classified to nodes of a reference taxonomy, the reference taxonomy not based on genetic distances, the nodes of the reference taxonomy representing genome classifications, the nodes of the reference taxonomy having unique reference IDs, wherein IDs means identifications;

provide a sample database comprising sample genomes that includes genomes of the one or more microorganisms, calculate genetic distances of the sample genomes, thereby forming a distance matrix;

calculate a self-consistent taxonomy using the distance matrix;

construct a k-mer database wherein k-mers of the sample genomes are assigned to nodes of the self-consistent taxonomy, the nodes of the self-consistent taxonomy assigned respective unique self-consistent IDs, and each of the k-mers of the sample genomes linked to one self-consistent ID;

map the reference IDs of the reference taxonomy to the self-consistent IDs of the self-consistent taxonomy, wherein each of the self-consistent IDs is linked to 1 or more of the mapped reference IDs; and calculating respective weights and/or respective probabilities of the mapped reference IDs based on number of nodes of the self-consistent taxonomy linked to each of the mapped reference IDs, wherein each of the mapped reference IDs of a given node of the self-consistent taxonomy is assigned a calculated weight and/or a calculated probability;

wherein the self-consistent k-mer database is stored on a computer readable medium, and the self-consistent k-mer database is capable of being queried for taxonomic profiling of sequenced nucleic acids when electronically linked to a computer system.

Further disclosed is a system comprising one or more computer processor circuits configured and arranged to:

access a self-consistent k-mer database for taxonomic profiling of a sequenced nucleic acids of a sample containing one or more organisms, the self-consistent k-mer database comprising:

i) k-mers of the sequenced nucleic acids, ii) respective self-consistent IDs assigned to the k-mers, the self-consistent IDs representing nodes of a self-consistent taxonomy, the self-consistent taxonomy calculated based on genetic distances of the one or more organisms, wherein IDs means identifications, iii) 1 or more reference IDs associated with each of the self-consistent IDs, the reference IDs representing nodes of a reference taxonomy not based on genetic distances of the one or more organisms, and iv) respective weights and/or respective probabilities linked to the 1 or more reference IDs; wherein the self-consistent k-mer database is stored on a computer readable medium.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

FIG. 6 is a sample of tabulated probabilistic report data available after k-mer analysis of sample data using the self-consistent k-mer database.

FIGS. 8A-8G depict a flow diagram for a process of profiling nucleic acids of a sample using the self-consistent k-mer database.

DETAILED DESCRIPTION

Figure 1:
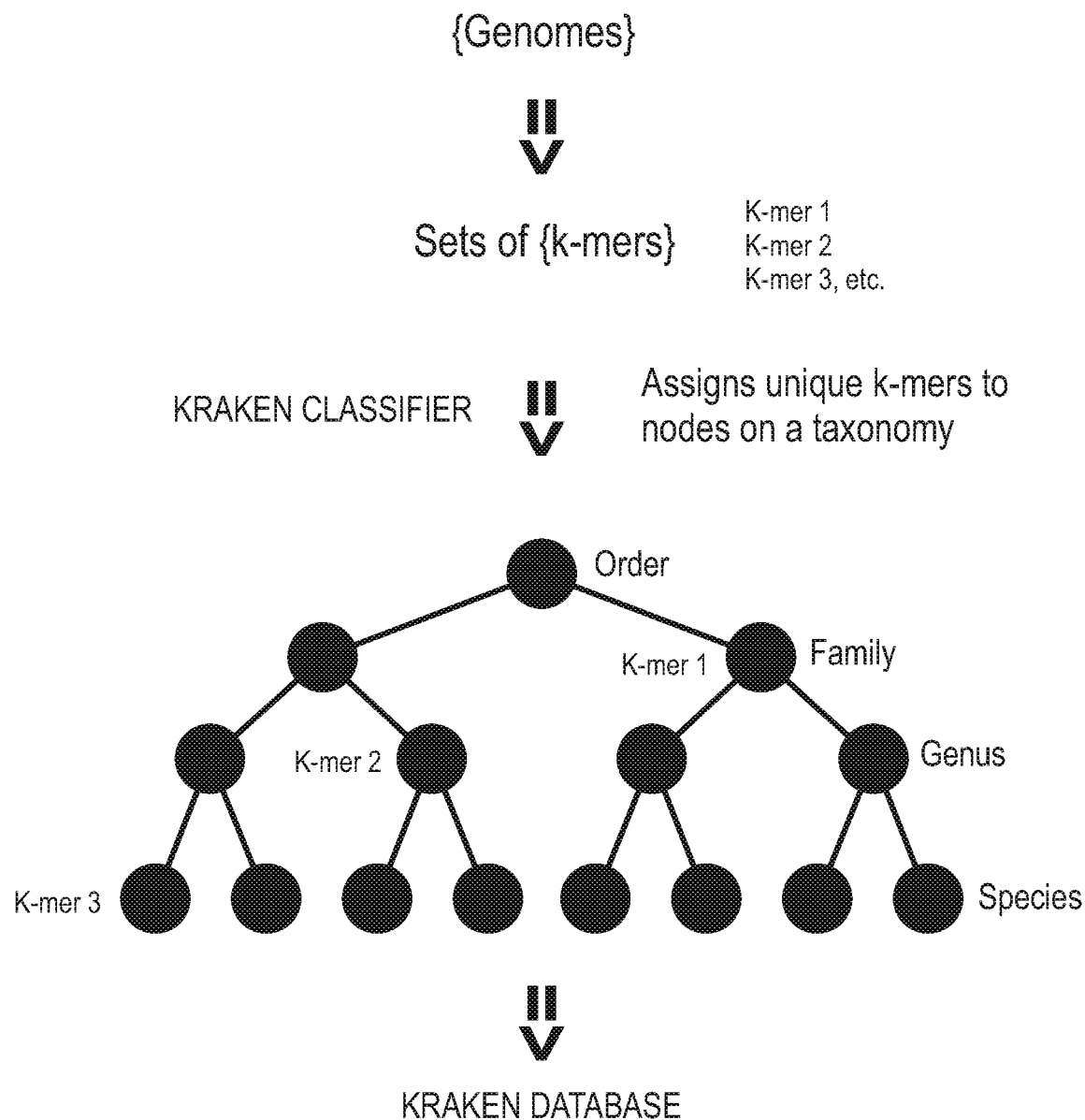
FIG. 1 is a diagram showing an existing process of classifying sequence reads.

Disclosed are self-consistent k-mer databases comprising k-mers of sequenced DNA and/or RNA of one or more organisms. K-mers are nucleotide sequences having a length k in nucleotide residues, where k is a positive integer in the range of about 10 to about 1000. The k-mers of the self-consistent k-mer databases are classified using a self-consistent taxonomy. The organisms can be eukaryotic or prokaryotic, preferably prokaryotic microorganisms. The self-consistent taxonomy is based on calculated genetic distances of genomes. In the present work, the genomes were assembled from raw sequences downloaded from the SRA at the NCBI website. The k-mers of the self-consistent k-mer database are assigned self-consistent identifications (abbreviated as self-consistent IDs), which represent nodes (i.e., taxa) of the self-consistent taxonomic tree.

Also disclosed are methods of generating a self-consistent k-mer database having a self-consistent taxonomy while preserving links to a not-self-consistent taxonomy of a reference k-mer database. Herein, the reference k-mer database is a data file containing k-mers from approximately 7000 genomes of the RefSeq Complete NCBI database of reference sequences. RefSeq Complete is a curated, non-redundant set including genomic DNA contigs, mRNAs and proteins for known genes, and entire chromosomes. The k-mers of the reference k-mer database were classified at NCBI using a not-self-consistent taxonomy (also referred to herein as reference taxonomy). The k-mers of the reference k-mer database (RefSeq Complete) have reference identifications (abbreviated as reference IDs) that represent nodes of the reference taxonomic tree (i.e., the standard NCBI taxonomy). It is known that at least one k-mer of the reference k-mer database has been misclassified (i.e., the k-mer was incorrectly assigned a reference ID associating the k-mer with the wrong node). Misclassifications of k-mers in the reference taxonomy can occur due to many factors, including metadata errors entered manually and even errors in the NCBI taxonomy. Occasionally, NCBI finds errors and revises the NCBI taxonomy.

The self-consistent k-mer database comprises a map that links the self-consistent IDs of the self-consistent taxonomy to the reference IDs of the reference taxonomy, thereby preserving the reference taxonomic labeling while remaining insensitive to the errors of the reference taxonomy.

Definitions

The following definitions are applicable.

Abbreviations A, C, G, and T refer to nucleotide bases adenine, cytosine, guanine, and thymine, respectively.

A "clade" is a group of biological taxa (such as species) that includes all descendants of one common ancestor.

A "contig" is a set of overlapping DNA sequences that together represent a consensus sequence of DNA or a region thereof.

A "consensus sequence" is the calculated order of the most frequent residues found at each position in a sequence alignment.

"Copy number" means the number of copies of a gene or plasmid within a genome. The copy number can vary from individual to individual.

"Coverage" or "depth of coverage" is the number of times a given sequence from a genome is represented in the set of sequences derived from that genome.

"DNA" is deoxyribonucleic acid.

A "protein domain" is a region of a protein having a particular shape and/or function.

A "gene" is the basic unit of heredity, a linear sequence of nucleotides along a segment of DNA that provides the coded instructions for synthesis of RNA, which, when translated into protein, leads to the expression of a hereditary trait.

"Genetic distance" is a quantitative measure of the divergence of one or more regions of DNA and/or RNA between species or populations of species. Genetic distance can be based on whole genome-whole genome distances, gene-gene distances, protein domain-protein domain distances (i.e., the portions of the DNA encoding for a particular protein domain), protein-protein distances (i.e., the portions of the DNA encoding for a whole protein), or protein domain-protein domain distances based on an amino acid distance metric. More specifically, genetic distance is a measure of the differences in nucleotide sequences of the k-mers with respect to whole genomes, genes, and/or other genetic regions of interest. Thus, the average number of codon or nucleotide differences per gene can be a measure of genetic distance. For the present work, the genetic distance is a numeric distance calculated between each pair of genomes of the reference database using MASH (which utilizes the MinHash algorithm). The MinHash algorithm calculates distance from a Jaccard index. The Jaccard index is calculated from "sketches" of the k-mers, which are diagrams showing the similarity and differences between k-mers of the pair of genomes.

A "genome" is the total genetic content of a microorganism. In the case of bacteria, the genome is DNA.

A "ground truth dataset" is a dataset formed by direct observation (measured data) as opposed to data obtained by inference or assumption.

Herein "high-throughput sequencing" (HTS) is any method of sequencing a nucleic acid that is highly parallel and does not involve cloning the nucleic acid. A genome or metagenome is cut into a large number of fragments, and the fragments are sequenced in parallel.

"Homology" refers to the similarity of sequences (e.g., DNA, RNA, Protein, etc.) arising from a common ancestry.

"Hybridization" is the formation of double-stranded helix from single-stranded complimentary pairs of DNA and/or RNA by annealing.

The term "k-mer" means a sub-sequence of a read obtained through DNA sequencing having k number of nucleotide base units, where k is a positive whole number greater than 1.

Herein, a "database" is an electronic file for storing and retrieving data. Databases are also referred to herein as data tables. Data tables comprise rows and columns (i.e., fields) of data. The rows are formally called tuples or records. A data table comprises one or more records, each record comprising one or more defined fields having respective defined data types (e.g., text, numeric, date, time, memo, and so on) and defined field lengths where applicable. A working data table comprises at least one record containing data in one or more fields of the record. The data tables are located on data storage devices, which can be remote or local relative to the user input/output devices. A "database system" comprises at least one data table and a database management software program for managing the storage and retrieval of data to and from the data tables. The database management programs can be remote or local relative to the data tables and/or the end user. A Relational Database Management System (RDBMS) is a database management system (DBMS) that uses relational techniques for storing and retrieving data using data tables. A relational database system can have many data tables, and each data table can have multiple records and multiple fields within each record. A data table in a relational database system can be accessed using an index. An index is an ordered set of references (e.g., pointers) to the records or rows in a data table. The index is used to access each record in the file using a key (e.g., one or more of the fields of the record or attributes of the row). Without an index, finding information in a large data table would require a resource-intensive time-consuming scan (e.g., linearly) of each record of a table. Indexes provide a faster alternate technique of accessing data contained in one or more data tables that are linked by a common key. Users can create indexes on a table after the table is built. An index is based on one or more columns (fields) of a given table.

A "k-mer database" is a database in which a given record comprises a field for storing a k-mer of a nucleic acid sequence of one or more organisms. Another field of the record stores a taxonomic ID that associates the k-mer to a lowest common ancestor node (LCA) of a taxonomic tree. As will be described below in more detail, other fields of the record can store reference IDs to a reference taxonomy. Still other fields of the record can store metadata associated with the k-mer and/or the nucleic acid sequence from which the k-mer originated.

Kraken is a taxonomic classifier that assigns taxonomic labels to DNA sequences, including k-mers. Kraken uses k-mers from a sequence read to query a reference database containing k-mers from reference genomes (i.e., the genomes of RefSeq Complete at NCBI) for matches. The k-mers are mapped to the lowest common ancestor (LCA) of all genomes known to contain a given k-mer. Typically, the k value for a k-mer query is 31 but this value can be modified by the user. For typical queries, k can be a positive whole number in the range of about 10 to about 1000.

Herein, a "Kraken database" is an electronic file containing k-mers assigned to a taxonomic hierarchy by the Kraken classifier.

A "locus" (plural loci) is a position on a genome (e.g., gene, regulatory element, origin of replication).

A "metagenome" is all the genetic information of a sample.

"Metagenomics" is the analysis or study of metagenomes.

"Metatranscriptome" is the collection of all RNA transcripts of a sample.

"Metatranscriptomics" is the analysis or study of metatranscriptomes.

A "microbiome" is a community of microorganisms that inhabit a particular environment (e.g., microbes of the human gut), or a sample taken therefrom.

"Origin of replication" is the locus at which DNA replication begins.

Operational taxonomic units (OTUs) are used by taxonomy classifier systems (e.g., Kraken classifier) to categorize the k-mers based on sequence similarity. For example, in 16S rRNA metagenomics, OTUs are clusters of similar sequence variants of the bacterial 16S rRNA marker gene sequence. Each cluster represents a taxonomic unit of a bacterial species or genus depending on the sequence similarity threshold. Typically, OTU clusters are defined by a 97% identity threshold of the 16S gene sequences to distinguish bacteria at the genus level. Species separation requires a higher threshold of 98% or 99% sequence identity, or the use of exact sequence variants instead of OTU cluster.

A "plasmid" is a self-replicating extrachromosomal circular DNA that replicates independently of the bacterial chromosome and carries genes for functions not essential for growth.

"RNA" is ribonucleic acid.

"mRNA" refers to messenger RNA. The mRNA codes for amino acid sequences composing proteins.

"rRNA" refers to ribosomal RNA.

"tRNA" refers to transfer RNA. A tRNA transports a specific amino acid to a ribosome for synthesis of a protein.

An "RNA transcript" is an RNA produced through the process of transcription of DNA.

"Sample" means any sample containing DNA and/or RNA capable of undergoing analysis using the disclosed methods.

"Sequencing" refers to a process of determining the precise order of base residues (i.e., nucleotides) in a nucleic acid (e.g., DNA, RNA).

A "sequence" is a fragment of a nucleic acid (e.g., RNA, DNA) that has been sequenced (i.e., the order of the nucleotides bases is known).

A "sequence read" or "read" is a finite length or fragment of a nucleic acid that is output by a sequencing instrument. For example, a read from an Illumina sequencer is 100-150 base pairs in length today. Sequencing may also be done on "paired end" reads where two reads are connected by a spacer (that is not read), increasing the effective read length to 300 or more and covering a larger region of the genome.

A "sequence alignment" is a way of arranging sequences to identify regions of similarity, which may be a consequence of functional, structural, or evolutionary relationships between the sequences.

"Shotgun sequencing" is a quasi-random process in which a nucleic acid is broken up into many random smaller fragments that are individually sequenced. The sequences are ordered based on overlapping regions of genetic code and reassembled into the complete sequence of the nucleic acid.

"Taxonomy" is a biological scheme of classification of organisms. Herein, for bacteria, the hierarchy is domain, kingdom, division, phylum, class, order, family, genus, species, sub-species, and strain. Each of the foregoing classifications is a "rank" on the taxonomic tree.

A "taxonomic tree" herein is a data structure for classifying organisms. The taxonomic tree comprises nodes (i.e., taxa, singular taxon) that are grouped into "parent nodes" linked to "child nodes". Parent nodes are depicted above child nodes in the tree diagram. Child nodes are taxonomic descendants of parent nodes. For example, a genus (parent node) can be linked to two or more species (child nodes). The taxonomic tree can be rooted (i.e., known ancestral root) or unrooted (i.e., unknown ancestral root), bifurcating (i.e., two child nodes per parent node) or multi-furcating (i.e., more than two child nodes per parent node). Typically, the taxonomic tree is in the form of a "binary tree" (i.e., each parent node has two child nodes). A "leaf node" is a child node having no descendants (e.g., the species of a genus). In the self-consistent taxonomy, each leaf node has one genome. "Internal nodes" are all nodes other than the leaf nodes.

"Transcription" is the process of forming an RNA from a DNA template.

The abbreviation "bp" means "base-pair" (e.g., a read of 100-bp means that one DNA read has 100 nucleotides in the polymer chain.

"Miscalling" refers to a sequencing error where a nucleotide in a sequence read is different from the true nucleotide.

A quality value is an assigned value given to each nucleotide in a sequence read that reflects the likelihood of miscalling the nucleotide. The higher the quality value is, the lower the likelihood of miscalling.

A "reference genome" is a genome from the same species or close species that has already been sequenced.

"Mapping" a sequence read is a process of finding the position or coordinate of a sequence read on the reference genome.

A "perfect match prefix" is a k-mer of a sequence read that is identical to, or a perfect match to some equal-length k-mer(s) of the reference genome. The k-mer of the sequence read is used to initially anchor the sequence read on the reference genome.

Base substitution: After a sequence read is mapped to the reference genome, certain bases are different from the corresponding bases on the reference genome.

Insertion: Compared with the reference genome, some continuous bases are inserted between two adjacent bases on the sequence read.

Deletion: Compared with the reference genome, the sequence read loses some continuous bases.

INDEL: an insertion or deletion in a read when trying to find the best alignment of a read to a reference genome.

FIG. 1 is a diagram showing an existing process of classifying sequence reads using a Kraken classifier. A sample metagenome is sequenced, producing reads of varying base length. In a k-mer based classification method, a reference database is provided using a set of genomes and taxonomy provided by the user. The classifier program (e.g., Kraken classifier, CLARK classifier) scans each k-mer of a given read and consults a reference database (e.g., NCBI RefSeq Complete genomes) which can contain many genomes, for an exact match. During the database build step, all distinct k-mers in a genome set are collected into a (k-mer, taxonomic ID) pair, with the taxonomic ID being assigned from the genome's operational taxonomic unit (OTU) of the reference taxonomy. As distinct k-mers are often shared across multiple organisms (for example, in conserved regions), the individual classification method must provide a mechanism for resolving conflicts. "Conserved sequences" are similar or identical DNA or RNA sequences, which have been maintained by natural selection and are shared by species or within a genome. One method of resolving a conflict is to set a k-mer's taxonomic ID to the lowest common ancestor (LCA) of the two conflicting nodes of the reference taxonomy and reduce the level of taxonomy to the next higher node on the tree. This approach reduces the specificity of a given k-mer while retaining overall sensitivity. Herein, the specificity of a k-mer decreases by moving the k-mer to a higher rank on the taxonomic tree. Sensitivity decreases by increasing the number of nodes at the same rank.

As there are often multiple exact k-mer matches for a given read, the classifier must also resolve conflicts against the taxonomy. When a consensus decision is reached by the software program, taking into account configurable threshold options (e.g., the number of k-mers that must match), the k-mer is declared as either classified and given a taxonomic ID or remains unclassified. A consensus is defined by the majority (largest fraction) of k-mers matching a single or unique lineage. The classified k-mers are assigned to nodes on a taxonomic tree.

The "reference taxonomy" is defined herein as a not-self-consistent taxonomy. A not-self-consistent taxonomy is one in which classifications can be made based on conflicting, incomplete, and/or erroneous input, that cause k-mers to be misclassified. Conflicting inputs can include errors in metadata. Metadata are any supplemental information added to the records of a database (e.g., information about the taxonomic hierarchy, the k-mers, and/or the reads, and so on). The metadata can be introduced by either the programs operating on the reads, human operators of the programs, or both. The metadata can be used to compare a classification done by the classifier program (e.g., Kraken) with a classification assigned by some other method (e.g., the lab contributing the other metadata) for validation purposes and/or identifying inconsistencies and errors.

Figure 2:
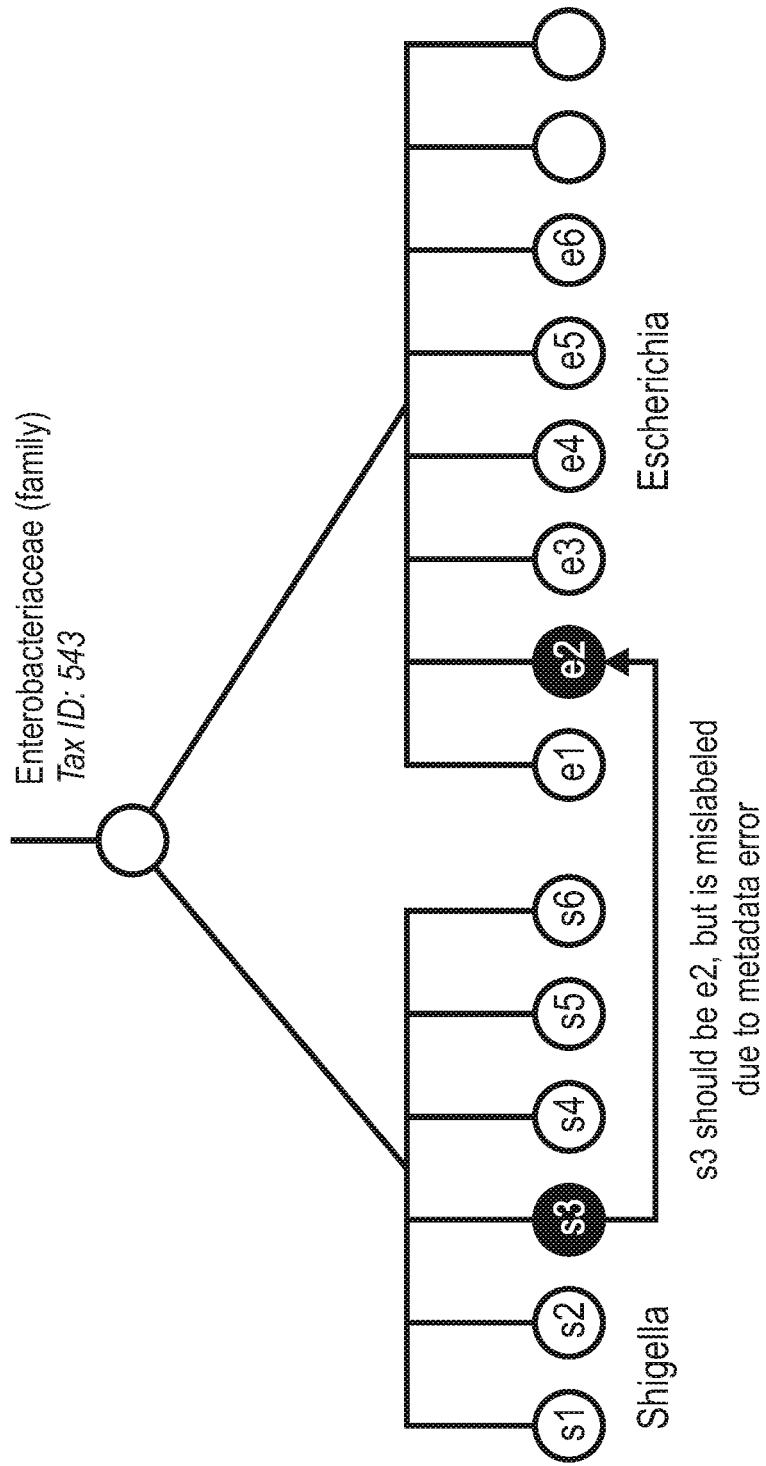
FIG. 2 is a diagram illustrating a partial taxonomic tree containing metadata errors.

FIG. 2 is a diagram illustrating a portion of a reference taxonomy (a not-self-consistent taxonomy) of a reference database containing metadata errors (e.g., the NCBI taxonomy of the genomes of RefSeq Complete). Metadata errors combined with a not-self-consistent taxonomy degrade the ability of a database system to assign a specific organism identification. Genomes at the leaf nodes of the reference taxonomy can be placed there based on manually added taxonomic IDs, which may be incorrect. In this example, the genome indicated as 's3' is incorrectly labeled as a *Shigella* genome and, based on that invalid metadata, placed with other *Shigella* genomes in the tree (indicated by the first character 's'). In fact, this hypothetical genome 's3' is an *Escherichia* genome. It "should be" labeled as *Escherichia* (e.g., 'e2') and placed on the tree with other *Escherichia* species, but it is not. Accordingly, node 'e2' is missing. The mislabeled *Escherichia* genome shares a large number of k-mers with all other *Escherichia* genomes, and when the database is built, k-mers that are shared by nodes at the same level or below on the tree are moved up to the lowest common ancestor (LCA) node (e.g., k-mers common to two or more species nodes move up to a common genus node). The node from which the k-mers move up retains only k-mers unique to that node. In this example, many of the k-mers that should be used to identify the genus *Escherichia* (and distinguish it from the genus *Shigella*) will move up to the Enterobacteriaceae family node in the tree, the LCA of the *Shigella* and *Escherichia* genera, causing a decrease in specificity of the k-mers moved up. This error greatly diminishes the ability of the reference database to identify the two organisms and increases the error in the identification capacity, which can render the information useless, for example, in disease diagnostics.

On the other hand, if the genomes are mapped to a self-consistent taxonomy, the problem with inaccurate or incorrect metadata can be separated from the k-mer classifications and construction of the k-mer database, thereby establishing an accurate classification for each k-mer. A self-consistent taxonomy is defined herein as a taxonomy constructed, preferably exclusively, from calculated genetic distances. Populations with many similar alleles have small genetic distances. This indicates that they are closely related and have a recent common ancestor.

A flow diagram for a method of constructing a k-mer database having a self-consistent taxonomy from a collection of genomes is shown in FIGS. 3A-3G.

Figure 3:
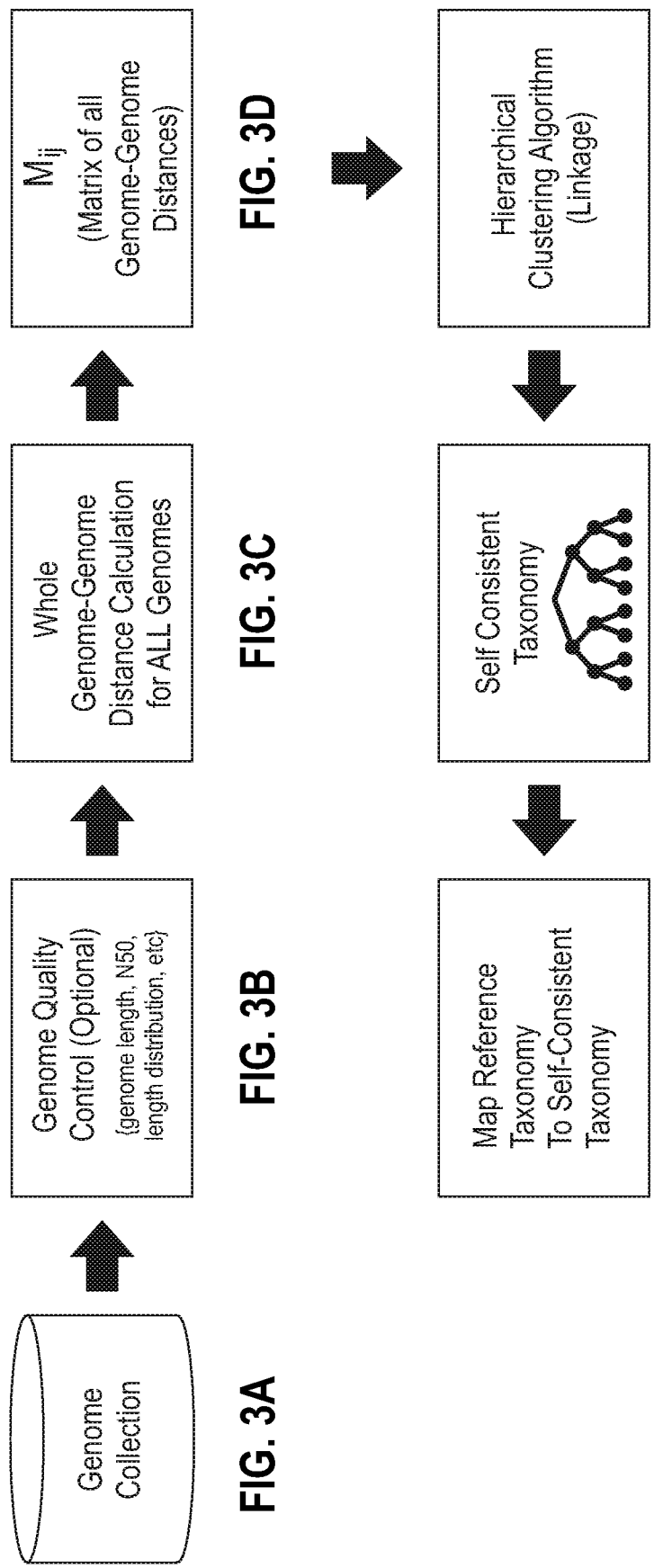
FIGS. 3A-3G depict a flow diagram for a method of constructing a self-consistent taxonomy from any collection of genomes.

The method begins by initially providing a collection of sequenced whole genomes (FIG. 3A). For the present work, the raw sequences of 360,000 prokaryote genomes were downloaded in December 2016 from the SRA at the NCBI website, and these were assembled into genomes. This collection of assembled genomes served as a "sample database" comprising "sample genomes." Almost half of the sample genomes had either metadata errors, misclassified reads, and/or were of poor quality due to other reasons. The sample genomes were treated as unclassified k-mers of nucleic acid for the following steps. It should be understood that the metadata in one or more of the sample genomes contained errors in classification in the reference taxonomy. The metadata of the sample genomes were carried forward into the genomes of the self-consistent k-mer database without affecting the node assignments of the sample genomes in the self-consistent taxonomy.

Optionally, quality control can be performed on the reads of the sample (FIG. 3B). Quality control can include, for example, the removal (trimming) of low-quality reads or segments of reads. Non-limiting trimming algorithms and software programs for cleanup of raw DNA sequence reads include SolexaQA DynamicTrim, FASTX-ToolKit, ConDeTri, NGS QC Toolkit, FASTQC, and Trimmamatic. For the present work, FASTQC and Trimmamatic were used on the genomes of the sample. The result was a "clean sample" containing 170,000 assembled genomes.

Next, the genetic distances were calculated for every pair of genomes of the clean sample (FIG. 3C). The result is a two-dimensional matrix M comprising genetic distances $m_{i,j}$ (FIG. 3D), where each element $m_{ij}$ is a calculated distance between genome i and genome j of the clean sample. Subscripts i and j are index values to each genome of the pair used to calculate distance $m_{ij}$. The distance between every genome and every other genome of the cleaned sample was calculated, resulting in matrix M. Non-limiting methods of calculating genetic distances include the MinHash method, the Meier-Kolthoff method, Cavalli-Sforza chord distance method, the Reynolds, Weir, and Cockerham method, Nei's standard genetic distance method, and pairwise distance method. Pairwise distance methods calculate distances based on differences between all pairs of k-mers in two datasets. For the present work, the genetic distances were calculated using the program MASH (github.com/marbl/Mash) using the MinHash algorithm (ONDOV, et al., "Mash: fast genome and metagenome distance estimation using MinHash," Genome Biology (2016), 17:132). MinHash calculates the distances between all pairs of genomes in the cleaned sample from k-mer "sketches." A sketch is a compressed representation of sequences that allows for tracking k-mer counts and k-mer frequency distributions of a sequence data set without storing the sequence structures themselves, thereby saving computer storage space and memory usage. The sketches are evaluated to produce a Jaccard index, which is used to calculate genetic distances between, in the present instance, pairs of genomes. The calculated distance matrix M for 170,000 genomes was over 5 gigabytes in size. The disclosed method is not limited to the use of MinHash for calculating the Jaccard index.

Classifying k-Mers to a Self-Consistent Taxonomy

The matrix M serves as input to a hierarchical agglomerative (bottom-up) or divisive (top-down) clustering algorithm (FIG. 3E) to compute a self-consistent taxonomy. For the present work, the clustering algorithm used was agglomerative single linkage (SLINK) using minimum spanning tree (MST) described respectively by Sibson, R., "SLINK: an optimally efficient algorithm for the single link cluster method," The Computer Journal, 1973, 16:30-34, and Rohlf, F. James, "Algorithm 76. Hierarchical clustering using the minimum spanning tree," The Computer Journal, 1973, 16:93-95. The clustering algorithm computes a new self-consistent taxonomy, which is independent of the reference taxonomy (i.e., the NCBI taxonomy) because it is based exclusively on the calculated genetic distance between the genomes of the clean sample (FIG. 3F). The self-consistent taxonomy is a binary tree. Each node of the self-consistent taxonomy is assigned a unique self-consistent ID. Each k-mer of the clean sample is assigned to one and only one node of the self-consistent taxonomy.

Other non-limiting agglomerative clustering algorithms include i) complete linkage (CLINK), ii) unweighted pair-group method using arithmetic averages (UPGMA, also called unweighted arithmetic average clustering), iii) weighted arithmetic average clustering (WPGMA, also referred to as "Mcquitty"), iv) Ward method, v) unweighted centroid clustering (UPGMC), and vi) weighted centroid clustering (WPGMC).

A non-limiting example of a divisive clustering algorithm is DIANA (Divisive Analysis Clustering).

In an embodiment, the self-consistent taxonomy is based on genome-genome distances calculated by MinHash. In another embodiment, the self-consistent taxonomy is based on genome-genome distances calculated by the Meier-Koltoff method. In another embodiment, the self-consistent taxonomy is based on genome-genome distances calculated by the Levenshtein distance method (also referred to as "edit distance" based on the number of edits required to convert one string (read) into another). In another embodiment, the self-consistent taxonomy is based on gene-gene distances in which sequence alignments to a known reference genome are performed by a software program MUSCLE (MUltiple Sequence Comparison by Log-Expectation), and genetic distance is calculated using Nei's standard genetic distance method or pairwise distance method.

MUSCLE is a multiple sequence alignment (MSA) software tool. MSA is generally the alignment of three or more biological sequences (protein or nucleic acid) of similar length. Other MSA software tools include Clustal Omega, Kalign, MAFFT, MView, MAFFT_addseq, T-Coffee, and WebPRANK.

Pairwise sequence alignment (PSA) is used to identify regions of similarity between two sequences. Pairwise sequence alignment tools include Needle and Stretcher for global (end-to end) alignment; Water, Matcher, and LALIGN for local alignment; and Genewise for genomic alignment. Other pairwise sequence alignment tools include and Promoterwise and Wise2dba.

Constructing a Self-Consistent k-Mer Database and Circumventing Metadata Errors

The self-consistent taxonomy is then used to construct a k-mer database (also referred to herein as a "self-consistent k-mer database) containing the k-mers of the clean sample associated with respective self-consistent IDs.

Mapping the Reference Taxonomy to the Self-Consistent Taxonomy

Next, a map is created associating the self-consistent IDs of the self-consistent taxonomy to the reference IDs of the reference taxonomy (FIG. 3G). In effect, this amounts to re-classifying the smaller number of genomes (k-mers) of the reference database (e.g., RefSeq Complete at NCBI) against the new self-consistent taxonomy while carrying forward the reference IDs and metadata of the reference taxonomy (i.e., standard NCBI taxonomy) into the self-consistent k-mer database. This process was accomplished using a custom software program. Every k-mer of the smaller reference database was assigned a node in the self-consistent taxonomy, thereby linking nodes of the new self-consistent taxonomy to named organisms of the reference taxonomy. Underlying child nodes of the self-consistent taxonomy that contained k-mers (i.e., of the 170,000 genomes) not present in the reference database (i.e., RefSeq Complete) were also linked to organisms of the reference taxonomy through interior nodes of the self-consistent tree.

Figure 4:
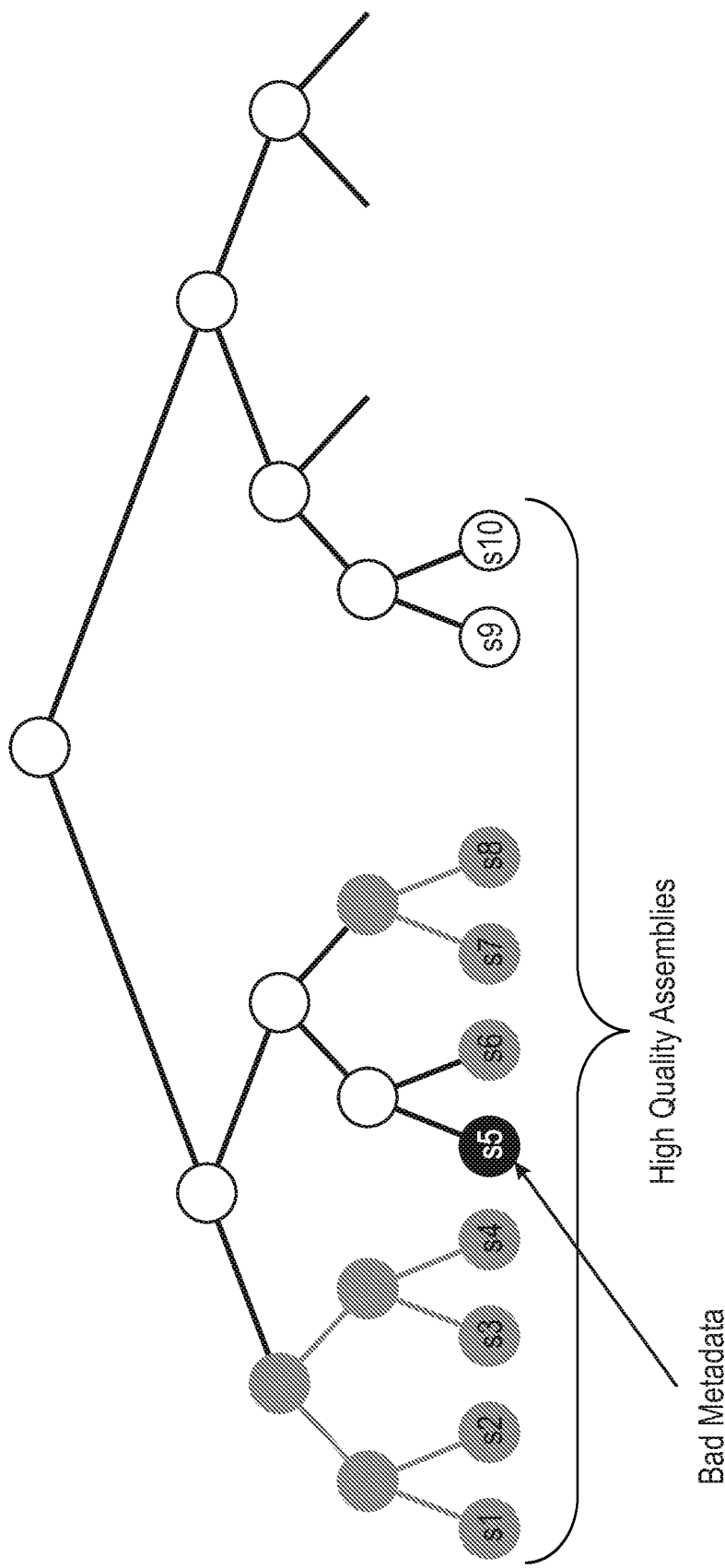
FIG. 4 is a portion of a tree diagram illustrating how a self-consistent taxonomy makes it possible to separate the problem of database construction from the problem of bad metadata. Although the $S_5$ genome contains bad metadata, the disclosed self-consistent taxonomy places the $S_5$ genome on the correct leaf node.

The self-consistent taxonomy circumvents misclassifications of the reference taxonomy as illustrated in the tree diagram of FIG. 4. Here, a series of genomes labeled s1-s4 and s6-s8 are clustered together in the self-consistent taxonomy because their genotypes are in fact similar to each other (e.g., they are all *Salmonella* genomes). The genome s5 has metadata that "label" it as *Escherichia*, but that information is not used to determine classification in the self-consistent taxonomy. Only the genetic distance is used, and since the genome s5 is in fact an example of a *Salmonella*, s5 becomes clustered with the other members of the *Salmonella* genus in the self-consistent taxonomy despite being incorrectly labeled in the metadata as *Escherichia*.

In the example of FIG. 4, the taxonomy is represented as a "binary tree", the typical output structure for a hierarchical clustering algorithm. In a binary tree structure, each parent node can have two child nodes. Each node of the self-consistent taxonomy is assigned a map relating a set of reportable reference IDs to that node's self-consistent ID. Leaf nodes in the reference binary tree (FIG. 4) have only one genome. Therefore, a given leaf node of the self-consistent taxonomy has only one reference ID mapping to one self-consistent ID. Higher level "parent nodes" (interior nodes) of the self-consistent taxonomy, identified by a single unique self-consistent ID, contain a "taxonomy map", which links each reference ID found below a given parent node with the number of child nodes in which that reference ID occurs.

In summary, a given record of the self-consistent k-mer database comprises a k-mer, a self-consistent ID assigned to the k-mer, one or more reference IDs of the reference taxonomy mapped to the self-consistent IDs of the self-consistent taxonomy, respective weights and/or respective probabilities of each of the reference IDs, and other optional data of the reference database if desired.

Condensing the Taxonomy

With this mapping, it is possible (optionally) to condense the tree in every place where the metadata are consistent with the self-consistent taxonomy and pairs of nodes within the binary tree have the same reference ID. Any node whose taxonomy map contains one and only one reference ID can be trimmed so long as its parent node contains one and only one reference ID. This effectively condenses the tree by combining all similar genomes with the same reference ID onto one node. It also preserves the child node "count" that reflects the quantitative weight of evidence below a given parent node. After this condensation step, a given node on the tree has its own unique self-consistent ID and a taxonomy map associating each reference ID with a weight equal to the number of genomes with that reference ID at or below the given node. The mapping is illustrated in Table 1. Each weight of Table 1 can have a whole number value greater than or equal to 1. Subscripts a, b, and c of Table 1 refer to different nodes of the self-consistent taxonomy, with correspondingly uniquely assigned self-consistent IDs. Similarly, subscripts i, j, k, x, y, and w of Table 1 refer to different nodes of the reference taxonomy, with correspondingly uniquely assigned reference IDs and their calculated weights.

for correction in order to increase accuracy of the self-consistent k-mer database. Moreover, the self-consistent k-mer database can be designed to be sensitive to specific reference taxon levels by collapsing or expanding taxon nodes based on common reference IDs.

Reporting

FIG. 6 is a sample of tabulated probabilistic report data available after k-mer analysis of sample data using the self-consistent k-mer database. The first column in the report table contains the self-consistent IDs of the database, and the second column contains the number of k-mers (or, alternatively, number of reads), assigned to each self-consistent ID. The subsequent columns are paired and enumerate all of the reference IDs linked to each self-consistent ID along with the probability assigned to each of the linked reference IDs. If there is only one linked reference ID, its probability is 1.0. If there are multiple linked reference IDs, then their probabilities add to 1.0.

TABLE 1

| self-consistent $ID_a$ | reference $ID_i$ | weight$_i$ | reference $ID_j$ | weight$_j$ | reference $ID_k$ | weight$_k$ |
|---|---|---|---|---|---|---|
| self-consistent $ID_b$ | reference $ID_x$ | weight$_x$ | | | | |
| self-consistent $ID_c$ | reference $ID_y$ | weight$_y$ | reference $ID_w$ | weight$_w$ | | |

As a non-limiting example, a self-consistent k-mer database designed to identify organisms at the species level can have a high level parent node having 1000 linked child nodes all containing the reference ID of one single species (e.g., *Salmonella enterica*). In this instance, the 1000 linked child nodes of the self-consistent k-mer database can be removed, leaving the high level parent node linked to a reference ID for *Salmonella enterica* having a weight of 1000.

Figure 5:
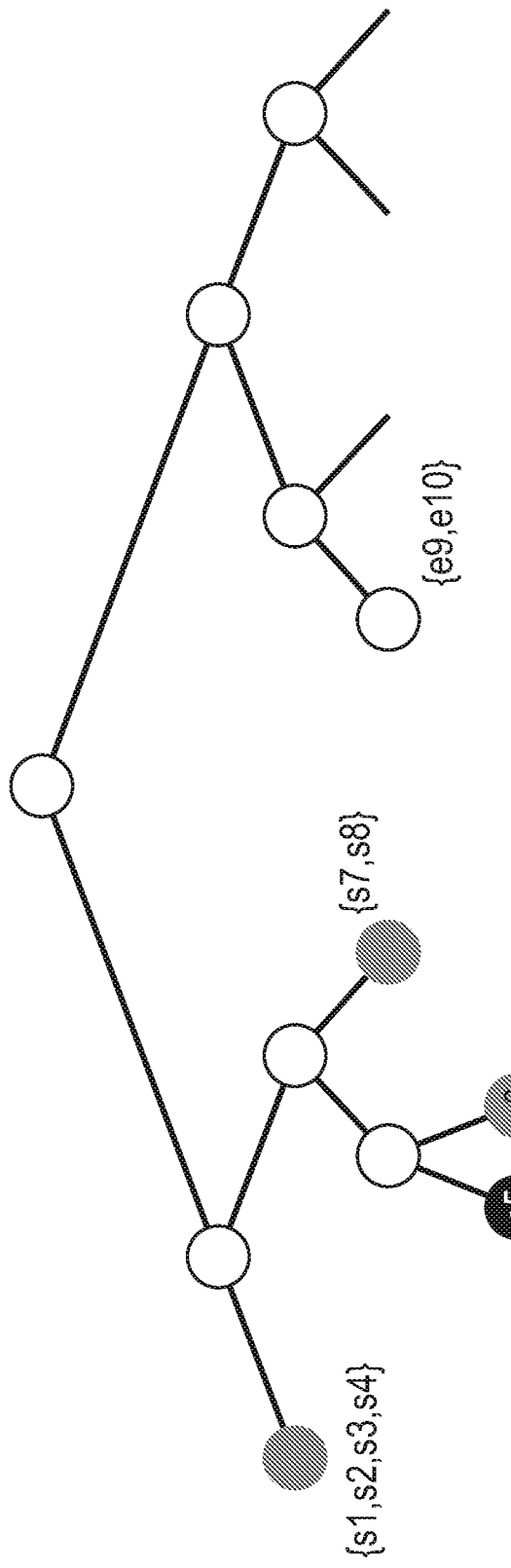
FIG. 5 is a portion of a tree diagram illustrating condensation of nodes of the taxonomic tree when the database utilizes self-consistent taxonomic IDs. The taxonomy can be condensed, taking advantage of every place a reference taxonomy is correct, by grouping all leaf nodes with common reference IDs onto one tree node.

An important feature of this approach to condensation is that it takes advantage of every place the self-consistent taxonomy is in agreement with the reference taxonomy and yet is robust against errors of the reference taxonomy. FIG. 5 again shows genome s5, which is *Salmonella* but is incorrectly labeled as *Escherichia*. Using the method described above, if this error is left uncorrected then that part of the taxonomic tree is left expanded. This means the unique k-mers do not move up to a higher taxonomic level (e.g., lowest common ancestor), thereby preserving the specificity of the database with respect to the self-consistent taxonomy. When the database is used to identify organisms within a metagenomic sample, the evidence for all possible reference IDs is reported based on the weights associated with that ID. In the case of a sample containing *Salmonella enterica*, the reads with k-mers unique to *Salmonella enterica* will be reported (post-process) in the reference taxonomy as the reference ID for *Salmonella enterica* with a weight of 1000, and *Escherichia* with a weight of 1. The probability of *Salmonella enterica* is then 1000/1001 while the probability of some *Escherichia* strain is only 1/1000. Thus the database report is robust against errors in the metadata. Database performance can be further improved by correcting those metadata errors.

Discontinuities of the reference taxon mapping in the self-consistent taxonomy can be favorably used to identify clerical errors and/or apparent errors of the metadata of the reference databases, reveal inaccuracies in the reference taxonomy structure, discover gene movement between organisms (i.e., horizontal gene transfer) that re-orients the organism into a new taxon category, and/or highlight areas of the taxon and database construction that needs attention Reporting can then be done by providing a probabilistic report such as, for example, the product of each reference ID probability with the k-mer or read count for each reference ID, and totaling by reference ID for all IDs, or by applying other rules (e.g., summing only the reference IDs with greatest probability at each self-consistent ID.

Taxonomic Profiling Using the Self-Consistent k-Mer Database

This section describes a method of profiling nucleic acids of a sample using the self-consistent k-mer database, preferably in conjunction with a computer system. The method is depicted in the flow diagram of FIGS. 8A-8G.

A sample is provided for analysis containing nucleic acids of one or more organisms therein (FIG. 8A). The nucleic acids can be of eukaryotic and/or prokaryotic origin. In an embodiment, the sample comprises nucleic acids of one or more prokaryotic microorganisms. Non-limiting examples of samples include water samples obtained from tap water, lakes, streams, field runoff, and sewage; swabbed samples from contact surfaces (e.g., building surfaces, countertops, furniture, utensils, clinical instruments, computer hardware, cell phones, door handles, doors, windows, screens, cabinets, cabinet doors, sinks, faucet); animal samples (e.g., blood, blood plasma, serum, cells, a cellular extract, a cellular aspirate, expectorant, sputum, saliva, mucous, urine, sweat, tears); and samples obtained from food, food-handling equipment, and surfaces contacted by food. The samples can be a solid or liquid containing water or no water.

RNA and/or DNA can be extracted from the working sample and subjected to high throughput sequencing (FIG. 8B).

Optionally, quality control of sequence data of the working sample is performed by removing data of poor quality, removing sequences introduced by the sequencing methodology, and/or removing any contaminating sequences (FIG. 8C).

Optionally, the sequences are assembled to contigs (FIG. 8D). K-mers of the sequences/contigs are then mapped to the genomes of the self-consistent k-mer database (FIG. 8E). The contigs can be mapped to the reference genome using Burrows-Wheeler transformation based method or a similar technique.

The per-position-coverage and windows of the mapped sequences or mapped contigs are then determined (FIG. 8F). Coverage thresholds for the mapped sequences or mapped contigs are then calculated. Optionally, the mapped sequences or mapped contigs can be filtered based on coverage threshold. Optionally, the sequence coverage data can be smoothed using a generic method (e.g., LOESS) to remove coverage spikes arising from technical biases. A more specialized method that takes into account specific genome characteristics can also be used if that information is available. From the coverage data, at least one organism of the sample is identified (FIG. 8G).

Metagenomic and metatranscriptomic sequences obtained by high throughput sequencing of an environmental sample can be passed to publicly available intermediary programs such as BLAST for aligning k-mers of the sequences of the environmental sample to the k-mers of the self-consistent k-mer database, thereby identifying which organisms of the self-consistent taxonomy, if any, are most likely to be present in the sample. Optionally, the intermediary program can conduct alignment of sequence data of the sample to raw sequences, contigs, and/or whole genomes from which the k-mers of the self-consistent k-mer database originated in order to increase specificity of the organism identification. The intermediary program can perform a simple database search on a sample sequence, or alternatively, conduct pairwise sequence alignments, multiple sequence alignments, and/or pairwise genome alignments.

Other non-limiting software programs for aligning metagenomic and metatranscriptomic sequences to the sequence data of the self-consistent taxonomy include FASTA (simple search), ALLALIGN (pairwise, multiple alignments), BLASTZ (pairwise), DNASTAR (pairwise, multiple), AVID (pairwise genome), GMAP (genome alignment), and MGA (multiple genome alignment).

Queries

This section generally applies to searches other than for classification purposes. For comparison, in a Kraken classification search, the data to be classified (e.g., a read) is processed to extract from it every k-mer in the read. Each k-mer is then compared to the entire reference k-mer database and if there is a hit, then a counter representing evidence for the taxonomic ID of the node it hits is incremented. When this is complete, the total hits from all k-mers are tallied and summarized in a report by node ID. Any k-mer in the read but not in the database is tallied as "not found."

In a search other than for classification purposes, queries can be performed on metadata information (e.g., author, date, source of the sequences, etc.), the k-mers, on the nucleic acid sequences from which the k-mers originated, on contigs of the nucleic acid sequences, on whole genomes assembled from the sequences, and/or on combinations of any of the foregoing. The k-mers, the nucleic acid sequences, the contigs, and the whole genomes can be stored in the same data table or in separate electronic files (e.g., text files such as FASTA or compressed text files such as FASTQ) that are relationally linked by index keys (e.g., the self-consistent IDs). No restriction is placed on the types of queries that can be performed, providing the queries do not exceed the limits of the information contained in the self-consistent k-mer database and any additional tables linked thereto. Queries can be performed by manual entry of search terms, by search terms generated programmatically, or by combinations thereof.

The self-consistent k-mer database can be located at sites available to the general public and/or to specialized groups (e.g., academic, medical, forensic, environmental, governmental, and/or military). Sites include private, corporate, and/or public websites for conducting online searches. Alternatively, the self-consistent k-mer database and linked additional tables can be downloaded and stored at a local site for conducting queries using a local computer network.

Searches can be conducted at a low level using the database management software used to create the database files, opening the self-consistent k-mer database and any additional linked tables manually and searching the opened files using command statements entered manually. Preferably, searches are performed using an intermediary software program designed to collect search terms using a graphical user interface, programmatically organize the search terms into valid query statements, open the database files, conduct searches on the database files based on the query statements, and report the results in an organized format, which can be in the form of an electronic file stored to a storage device, data displayed on a monitor, data sent to an output device (e.g., printer), and/or data passed to another program for further analysis and/or handling.

Microorganisms

Microorganisms include bacteria, fungi, viruses, protozoans, and parasites.

Bacterial species can be Gram-positive or Gram-negative. Exemplary non-limiting bacterial species include *Acetobacter aurantius, Acinetobacter baumannii, Actinomyces israelii, Agrobacterium radiobacter, Agrobacterium tumefaciens, Anaplasma phagocytophilum, Azorhizobium caulinodans, Azotobacter vinelandii, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacillus Thuringiensis, Bacteroides fragilis, Bacteroides gingivalis, Bacteroides melaninogenicus* (also known as *Prevotella melaninogenica*), *Bartonella henselae, Bartonella quintana, Bordetella, Bordetella bronchiseptica, Bordetella pertussis, Borrelia afzelii, Borrelia burgdorferi, Borrelia garinii, Borrelia recurrentis, Brucella abortus, Brucella canis, Brucella melitensis, Brucella suis, Burkholderia mallei, Burkholderia pseudomallei, Burkholderia cepacia, Calymmatobacterium granulomatis, Campylobacter, Campylobacter coli, Campylobacter fetus, Campylobacter jejuni, Campylobacter pylori, Chlamydophila pneumoniae* (previously called *Chlamydia pneumoniae*), *Chlamydophila psittaci* (previously called *Chlamydia psittaci*), *Chlamydia trachomatis, Clostridium botulinum, Clostridium difficile, Clostridium perfringens* (previously called *Clostridium welchii*), *Clostridium tetani, Corynebacterium diphtheriae, Corynebacterium fusiforme, Coxiella burnetii, Ehrlichia canis, Ehrlichia chaffeensis, Enterobacter cloacae, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus bulgaricus, Lactobacillus casei, Lactococcus lactis, Legionella pneumophila, Leptospira interrogans, Leptospira santarosai, Leptospira weilii, Leptospira noguchii, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegma-* tis, *Mycobacterium tuberculosis, Mycobacterium ulcerans, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Prevotella melaninogenica* (previously called *Bacteroides melaninogenicus*), *Pseudomonas aeruginosa, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Shigella sonnei, Spirillum volutans, Streptococcus agalactiae, Staphylococcus aureus, Staphylococcus epidermidis, Staphylococcus saprophyticus, Stenotrophomonas maltophilia, Streptococcus agalactiae, Streptococcus avium, Streptococcus bovis, Streptococcus cricetus, Streptococcus faceium, Streptococcus faecalis, Streptococcus ferns, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Streptococcus viridans, Treponema pallidum, Treponema denticola, Ureaplasma urealyticum, Vibrio cholerae, Vibrio comma, Vibrio parahaemolyticus, Vibrio vulnificus, Yersinia enterocolitica, Yersinia pestis, Yersinia pseudotuberculosis,*

Non-limiting exemplary viruses include the family Retroviridae, such as human deficiency viruses, such as HIV-I (also referred to as HTLV-III), HIV-II, LAC, IDLV-III/LAV, HIV-III or other isolates such as HIV-LP, the family Picornaviridae, such as poliovirus, hepatitis A, enteroviruses, human Coxsackie viruses, rhinoviruses, echoviruses, the family Calciviridae, such as viruses that cause gastroenteritis, the family Togaviridae, such as equine encephalitis viruses and rubella viruses, the family Flaviviridae, such as dengue viruses, encephalitis viruses and yellow fever viruses, the family Coronaviridae, such as coronaviruses, the family Rhabdoviridae, such as vesicular stomata viruses and rabies viruses, the family Filoviridae, such as Ebola viruses, the family Paramyxoviridae, such as parainfluenza viruses, mumps viruses, measles virus and respiratory syncytial virus, the family Orthomyxoviridae, such as influenza viruses, the family Bungaviridae, such as Hataan viruses, bunga viruses, phleoboviruses and Nairo viruses, the family Arena viridae, such as hemorrhagic fever viruses, the family Reoviridae, such as reoviruses, orbiviruses and rotaviruses, the family Bimaviridae, the family Hepadnaviridae, such as hepatitis B virus, the family Parvoviridae, such as parvoviruses, the Papovaviridae, such as papilloma viruses and polyoma viruses, the family Adenoviridae, such as adenoviruses, the family Herpesviridae, such as herpes simplex virus (HSV) I and II, varicella zoster virus and pox viruses, or the family Iridoviridae, such as African swine fever virus). The virus can be an unclassified virus, such as the etiologic agents of Spongiform encephalopathies, the agent of delta hepatitis, the agents of non-A, non-B hepatitis (class 1 enterally transmitted; class 2 parenterally transmitted such as Hepatitis C); Norwalk and related viruses and astroviruses.

Other non-limiting exemplary viruses include Varicella-zoster virus, Epstein-barr virus, Human cytomegalovirus, Human herpesvirus type 8, Human papillomavirus, BK virus, JC virus, Smallpox, Parvovirus B19, poliovirus, yellow fever virus, West Nile virus, TBE virus, Rubella virus, Hepatitis E virus, Influenza virus, Lassa virus, Crimean-Congo hemorrhagic fever virus, Hantaan virus, Marburg virus, Coltivirus, Banna virus, and zika virus.

Non-limiting exemplary fungi include *Candida albicans, Aspergillus fumigatus, Aspergillus flavus, Aspergillus clavatus, Cryptococcus neoformans, Cryptococcus laurentii, Cryptococcus albidus, Cryptococcus gattii, Histoplasma capsulatum, Pneumocystis jirovecii, Pneumocystis carinii,* and *Stachybotrys chartarurn.*

Non-limiting exemplary protozoa include *Entamoeba histolytica, Entamoeba coli, Entamoeba dispar, Entamoeba moshkovskii, Entamoeba bangladeshi, Entamoeba hartmanni, Dientamoeba fragilis, Endolimax nana, Lodarnoeba butschlii, Plasmodium malariae, Plasmodium falciparum, Plasmodium vivax, Plasmodium ovale, Naegleria fowleri, Acanthamoeba* species, *Balamuthia mandrillaris, Sappinia diploidea, Giardia larnblia, Giardia intestinalis, Giardia duodenalis, Toxoplasma gondii, Nippostrongylus brasiliensis, Cryptosporidium parvum, Cryptosporidium hominis, Cryptosporidium cams, Cryptosporidium felis, Cryptosporidium meleagridis, Cryptosporidium muris, Trichomonas vaginalis, Trypanosoma cruzi, Leishmania major, Leishmania tropica, Leishmania barziliensis, Leishmania mexicana, Leishmania guyanesis, Leishmania panamensis,* and *Trypanosoma brucei.*

Sequencing

Non-limiting methods of DNA/RNA sequencing include massively parallel signature sequencing (or MPSS), Polony sequencing, 454 pyrosequencing method, Illumina (Solexa) sequencing, SOLiD sequencing, ion semiconductor sequencing, DNA nanoball sequencing, heliscope sequencing, single molecule real time sequencing (SMRT sequencing), solid state nanopore sequencing, protein based nanopore sequencing, sequencing by electrical tunneling currents, sequencing by matrix-assisted laser desorption ionization time-of-flight mass spectrometry (MALDI-TOF MS), microfluidic Sanger sequencing, transmission electron microscopy DNA sequencing, RNA polymerase (RNAP) sequencing method, in vitro virus high throughput sequencing (IVV-HiTSeq), and sequencing by hybridization. Multiple fragmented sequence reads can be assembled together by software on the basis of their overlapping areas.

The foregoing methods of sequencing can be used singularly or in combination. The sequencing methods can be applied to genome sequencing, genome resequencing, transcriptome profiling (RNA-Seq), DNA-protein interactions (ChIP-sequencing), and epigenome characterization. Preferably, the sequencing method(s) operates in a parallel mode (characterizing many sequences concurrently).

Computer Hardware and Software

The computer system for implementing the present invention can take the form of an entirely hardware embodiment, an entirely software embodiment (including firmware, resident software, microcode, etc.), or a combination of software and hardware that may all generally be referred to herein as a "circuit," "module," or "system."

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 7:
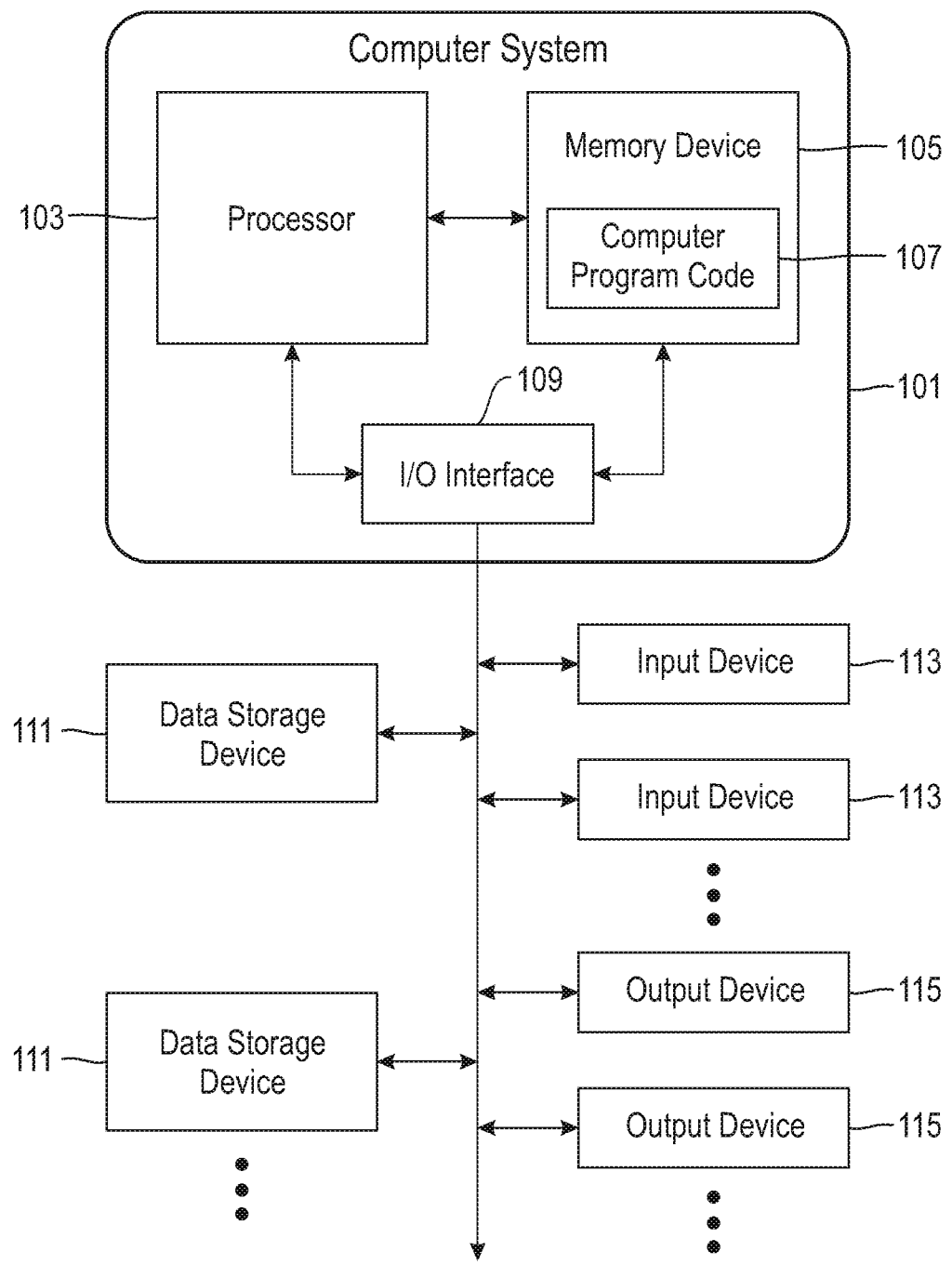
FIG. 7 is a block diagram showing a structure of a computer system and computer program code that may be used to implement a method of processing, including natural-language processing, to generate a disclosed self-consistent k-mer database from a reference k-mer database containing misclassified sequence data.

FIG. 7 shows a structure of a computer system and computer program code that may be used to implement a method of processing, including natural-language processing, to generate a disclosed self-consistent k-mer database from a reference k-mer database containing misclassified sequence data. The computer system and program code can also be used to implement a method of processing, including natural-language processing, utilizing the self-consistent k-mer database to conduct taxonomic profiling of samples containing one or more organisms.

In FIG. 7, computer system 101 comprises a processor 103 coupled through one or more I/O Interfaces 109 to one or more hardware data storage devices 111 and one or more I/O devices 113 and 115. Hardware data storage devices 111 can contain the reference k-mer database and/or the self-consistent k-mer database.

Hardware data storage devices 111 may include, but are not limited to, magnetic tape drives, fixed or removable hard disks, optical discs, storage-equipped mobile devices, and solid-state random-access or read-only storage devices. I/O devices may comprise, but are not limited to: input devices 113, such as keyboards, scanners, handheld telecommunications devices, touch-sensitive displays, tablets, biometric readers, joysticks, trackballs, or computer mice; and output devices 115, which may comprise, but are not limited to printers, plotters, tablets, mobile telephones, displays, or sound-producing devices. Data storage devices 111, input devices 113, and output devices 115 may be located either locally or at remote sites from which they are connected to I/O Interface 109 through a network interface.

Processor 103 may also be connected to one or more memory devices 105, which may include, but are not limited to, Dynamic RANI (DRAM), Static RANI (SRAM), Programmable Read-Only Memory (PROM), Field-Programmable Gate Arrays (FPGA), Secure Digital memory cards, SIM cards, or other types of memory devices.

At least one memory device 105 contains stored computer program code 107, which is a computer program that comprises computer-executable instructions. The stored computer program code can include a program for natural-language processing that implements the disclosed methods. The data storage devices 111 may store the computer program code 107. Computer program code 107 stored in the storage devices 111 can be configured to be executed by processor 103 via the memory devices 105. Processor 103 can execute the stored computer program code 107.

Thus the present invention discloses a process for supporting computer infrastructure, integrating, hosting, maintaining, and deploying computer-readable code into the computer system 101, wherein the code in combination with the computer system 101 is capable of performing the analysis of sequence data pertinent to the formation of the self-consistent k-mer database from a reference k-mer database, and generating reports therefrom. The computer system 101 is capable of performing the analysis of sequence data of a sample pertinent to the determination of identifying species using the self-consistent k-mer database.

Any of the components of the present invention can be created, integrated, hosted, maintained, deployed, managed, serviced, supported, etc. by a service provider. Thus, the present invention discloses a process for deploying or integrating computing infrastructure, comprising integrating computer-readable code into the computer system 101, wherein the code in combination with the computer system 101 is capable of performing the analysis of sequence data pertinent to the determination of identifying the viable species of the sample.

One or more data storage units 111 (or one or more additional memory devices not shown in FIG. 7) may be used as a computer-readable hardware storage device having a computer-readable program embodied therein and/or having other data stored therein, wherein the computer-readable program comprises stored computer program code 107. Generally, a computer program product (or, alternatively, an article of manufacture) of computer system 101 may comprise said computer-readable hardware storage device.

While it is understood that program code 107 may be deployed by manually loading the program code 107 directly into client, server, and proxy computers (not shown) by loading the program code 107 into a computer-readable storage medium (e.g., computer data storage device 111), program code 107 may also be automatically or semi-automatically deployed into computer system 101 by sending program code 107 to a central server (e.g., computer system 101) or to a group of central servers. Program code 107 may then be downloaded into client computers (not shown) that will execute program code 107.

Alternatively, program code 107 may be sent directly to the client computer via e-mail. Program code 107 may then either be detached to a directory on the client computer or loaded into a directory on the client computer by an e-mail option that selects a program that detaches program code 107 into the directory.

Another alternative is to send program code 107 directly to a directory on the client computer hard drive. If proxy servers are configured, the process selects the proxy server code, determines on which computers to place the proxy servers' code, transmits the proxy server code, and then installs the proxy server code on the proxy computer. Program code 107 is then transmitted to the proxy server and stored on the proxy server.

In one embodiment, program code 107 is integrated into a client, server and network environment by providing for program code 107 to coexist with software applications (not shown), operating systems (not shown) and network operating systems software (not shown) and then installing program code 107 on the clients and servers in the environment where program code 107 will function.

The first step of the aforementioned integration of code included in program code 107 is to identify any software on the clients and servers, including the network operating system (not shown), where program code 107 will be deployed that are required by program code 107 or that work in conjunction with program code 107. This identified software includes the network operating system, where the network operating system comprises software that enhances a basic operating system by adding networking features. Next, the software applications and version numbers are identified and compared to a list of software applications and correct version numbers that have been tested to work with program code 107. A software application that is missing or that does not match a correct version number is upgraded to the correct version.

A program instruction that passes parameters from program code 107 to a software application is checked to ensure that the instruction's parameter list matches a parameter list required by the program code 107. Conversely, a parameter passed by the software application to program code 107 is checked to ensure that the parameter matches a parameter required by program code 107. The client and server operating systems, including the network operating systems, are identified and compared to a list of operating systems, version numbers, and network software programs that have been tested to work with program code 107. An operating system, version number, or network software program that does not match an entry of the list of tested operating systems and version numbers is upgraded to the listed level on the client computers and upgraded to the listed level on the server computers.

After ensuring that the software, where program code 107 is to be deployed, is at a correct version level that has been tested to work with program code 107, the integration is completed by installing program code 107 on the clients and servers.

Embodiments of the present invention may be implemented as a method performed by a processor of a computer system, as a computer program product, as a computer system, or as a processor-performed process or service for supporting computer infrastructure. The disclosed self-consistent database can be located on a cloud platform of a computer network.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A method, comprising:
providing a reference database comprising reference k-mers, the reference k-mers derived from sequenced nucleic acids of one or more organisms, wherein the reference k-mers are classified to nodes of a reference taxonomy, the reference taxonomy not based on genetic distances, the nodes of the reference taxonomy representing genome classifications, the nodes of the reference taxonomy having unique reference IDs, wherein IDs means identifications;
providing a sample database comprising sample genomes that includes genomes of the one or more organisms;
calculating genetic distances of the sample genomes, thereby forming a distance matrix;
calculating a self-consistent taxonomy using the distance matrix;
constructing a self-consistent k-mer database comprising k-mers of the sample genomes, wherein the k-mers of the sample genomes are assigned to nodes of the self-consistent taxonomy based on genetic distance, the nodes of the self-consistent taxonomy assigned respective unique self-consistent IDs, and each of the k-mers of the sample genomes is linked to a respective one of the self-consistent IDs;
mapping the reference k-mers and associated reference IDs to the self-consistent k-mer database by storing, at each respective node of the self-consistent k-mer database, a 3-tuple comprising a k-mer, one or more respective reference IDs, and a single respective self-consistent ID, thereby linking reference IDs to self-consistent IDs, wherein each of the self-consistent IDs assigned to a leaf node of the self-consistent taxonomy is mapped to exactly one reference ID and each of the self-consistent IDs assigned to an internal node of the self-consistent taxonomy is mapped to each respective reference ID below the respective internal node;
calculating respective weights and/or respective probabilities of the mapped reference IDs based on the number of nodes of the self-consistent taxonomy linked to each of the mapped reference IDs, wherein each of the mapped reference IDs of a given node of the self-consistent taxonomy is assigned a calculated weight and/or a calculated probability;
compressing the self-consistent k-mer database by removing all nodes of the self-consistent k-mer database having one and only one reference ID so long as the respective parent node contains one and only one reference ID;
querying the self-consistent k-mer database for taxonomic profiling of a taxonomically unclassified k-mer of a sequenced nucleic acid; and
classifying the taxonomically unclassified k-mer to a node of the self-consistent k-mer database, wherein classifying the taxonomically unclassified k-mer comprises assigning both a self-consistent ID and a reference ID to the taxonomically unclassified k-mer.

2. The method of claim 1, wherein at least one of the k-mers of the reference database is misclassified in the reference taxonomy.

3. The method of claim 1, wherein at least one of the sample genomes is misclassified in the reference taxonomy.

4. The method of claim 1, wherein the method comprises condensing, into a single node, two or more nodes of the self-consistent taxonomy that share a common reference ID.

5. The method of claim 1, wherein the one or more organisms are prokaryotes.

6. The method of claim 1, wherein the self-consistent taxonomy is based exclusively on the calculated genetic distances.

7. The method of claim 1, wherein no two nodes of the self-consistent taxonomy are linked to an identical k-mer.

8. The method of claim 1, wherein the nodes of the self-consistent taxonomy comprise parent nodes linked to child nodes, and no two child nodes of a common parent node are linked to an identical reference ID.

9. The method of claim 1, wherein the genetic distances are selected from the group consisting of genome-genome distances, gene-gene distances, protein domain-protein domain distances, and protein-protein distances.

10. The method of claim 1, wherein the genetic distances are genome-genome distances calculated using the MinHash algorithm.

11. The method of claim 1, wherein the genetic distances are genome-genome distances calculated using the Meier-Koltoff algorithm.

12. The method of claim 1, wherein the genetic distances are gene-gene distances calculated using Nei's standard genetic distance.

13. The method of claim 1, wherein the genetic distances are gene-gene distances calculated using pairwise distance method.

14. The method of claim 1, wherein the genetic distances are protein domain-protein domain distances.

15. The method of claim 1, wherein the k-mers are assigned to nodes of the self-consistent taxonomy using an agglomerative hierarchical algorithm.

16. The method of claim 1, wherein the agglomerative hierarchical algorithm is selected from the group consisting of i) single linkage (SLINK), ii) complete linkage (CLINK), iii) unweighted pair-group method using arithmetic averages (UPGMA), iv) weighted arithmetic average clustering (WPGMA), v) Ward method, vi) unweighted centroid clustering (UPGMC) and vii) weighted centroid clustering (WPGMC).

17. A system comprising one or more computer processor circuits configured and arranged to:
  access a reference database comprising reference k-mers derived from sequenced nucleic acids of one or more organisms, wherein the reference k-mers are classified to nodes of a reference taxonomy, the reference taxonomy not based on genetic distances, the nodes of the reference taxonomy representing genome classifications, the nodes of the reference taxonomy having unique reference IDs, wherein IDs means identifications;
  access a sample database comprising sample genomes that includes genomes of the one or more organisms;
  calculate genetic distances of the sample genomes, thereby forming a distance matrix;
  calculate a self-consistent taxonomy using the distance matrix;
  construct a self-consistent k-mer database comprising k-mers of the sample genomes, wherein the k-mers of the sample genomes are assigned to nodes of the self-consistent taxonomy based on genetic distance, the nodes of the self-consistent taxonomy assigned respective unique self-consistent IDs, and each of the k-mers of the sample genomes is linked to a respective one of the self-consistent IDs;
  map the reference k-mers to the k-mers of the self-consistent k-mer database by storing, at each respective node of the self-consistent k-mer database, a 3-tuple comprising a k-mer, one or more respective reference IDs, and a respective self-consistent ID, thereby mapping reference IDs to self-consistent IDs, wherein each of the self-consistent IDs assigned to a leaf node of the self-consistent taxonomy is mapped to exactly one reference ID and each of the self-consistent IDs assigned to an internal node of the self-consistent taxonomy is mapped to each respective reference ID below the respective internal node;
  calculate respective weights and/or respective probabilities of the mapped reference IDs based on number of nodes of the self-consistent taxonomy linked to each of the mapped reference IDs, wherein each of the mapped reference IDs of a given node of the self-consistent taxonomy is assigned a calculated weight and/or a calculated probability;
  compress the self-consistent k-mer database by removing all nodes of the self-consistent k-mer database having one and only one reference ID so long as the respective parent node contains one and only one reference ID;
  query the self-consistent k-mer database for taxonomic profiling of a taxonomically unclassified k-mer of a sequenced nucleic acid; and
  classify the taxonomically unclassified k-mer to a node of the self-consistent k-mer database, wherein classifying the taxonomically unclassified k-mer comprises assigning both a self-consistent ID and a reference ID to the taxonomically unclassified k-mer.

18. The system of claim 17, wherein the system is capable of generating a report summarizing reference IDs mapped to the self-consistent IDs of the self-consistent k-mer database.

19. The system of claim 17, wherein the report lists reference IDs with respective weights.

* * * * *